United States Patent [19]
Paul

[11] Patent Number: 5,626,883
[45] Date of Patent: May 6, 1997

[54] ASCORBIC ACID COMPOSITIONS PROVIDING ENHANCED HUMAN IMMUNE SYSTEM ACTIVITY

[75] Inventor: Stephen M. Paul, Rancha Santa Margarita, Calif.

[73] Assignee: Metagenics, Inc.

[21] Appl. No.: 228,587

[22] Filed: Apr. 15, 1994

[51] Int. Cl.$^6$ .................. A01N 31/02; A01N 43/08; A01N 57/00; A01N 59/26

[52] U.S. Cl. .................. 424/605; 424/601; 424/606; 514/23; 514/25; 514/27; 514/28; 514/99; 514/336; 514/355; 514/400; 514/474; 514/476; 514/482; 514/491; 514/561; 514/562; 514/563; 514/564; 514/565; 514/566; 514/567; 514/724; 514/904; 514/905

[58] Field of Search .................. 514/23, 25, 27, 514/28, 99, 336, 355, 400, 474, 482, 561–567, 724, 904, 905, 476, 491; 424/606, 601, 605

[56] References Cited

U.S. PATENT DOCUMENTS 5,141,758  8/1992  Monte ........................................ 426/72
5,270,171  12/1993  Cercek et al. ............................. 435/29

OTHER PUBLICATIONS

Basu, T.K., *The Influence of Drugs with Particular Reference to Aspirin on the Bioavailability of Vitamin C*, Applied Science Publishers (1981).

Englard, S., Seifter, S., *The Biochemical Functions of Ascorbic Acid*, Annual Reviews, Inc. (1986).

O'Sullivan, K.R., Mathias, P.M., Beattie, S., Hamilton, H., O'Morain, C., Cahill, R.J., *Effects of vitamin antioxidant supplementation on cell kinetics of patients with adenomatous polyps*, Department of Gastroenterology, Meath and Adelaide Hospitals, Trinity College, Dublin, Ireland (Nov. 10, 1992).

Khan, P.K. and Sinha, S.P., *Antimutagenic efficacy of higher doses of vitamin C*, Mutation Research, 298 (1993) 157–161.

Ganguly, Ph.D., R., Durieus, M., Waldman, M.D., R. H., *Macrophage funtion in vitamin C–deficient guinea pigs;* The American Journal of Clinical Nutrition 29: Jul. 1976 pp. 762–765.

Keusch, Gerald T., Farthing, Michael J.G., *Nutrition and Infection*, Annual Review of Nutrition, pp. 131–147 (1986).

Barone, J., Taioli, E., Hebert, J.R., Wynder, E.L., Lawrence Fribaum Associates, Inc., *Vitamin Supplement Use and Risk for Oral and Esophageal Cancer*, Nutrition and Cancer, vol. 18 No. 1 (1992).

Schwartz, J., Weiss, S.T., *Relationship between dietary vitamin C intake and pulmonary function in the First National Health and Nutrition Examination Survey (NHANES I)*, American Journal of Clinical Nutrition 1994; 59:110–4.

Gershoff, Ph.D., S.N., *Vitamin C (ascorbic Acid): New Roles, New Requirements?*, Nutrition Reviews, vol. 51, No. 11, Nov. 1993:313–326.

Block, G., *Vitamin C and cancer prevention: the epidemiologic evidence*, American Journal of Clinical Nutrition 1991; 53;270S–82S.

Amabile–Cuevas, C.F., Pina–Zentella, R.M., Wah–Laborde, M.E., *Decreased resistance to antibiotics and plasmid loss in plasmid–carrying strains of Staphylococcus aureus treated with ascorbic acid*, Mutation Research, 264 (1991) 119–125.

Cahill, R.J., O'Sullivan, K.R., Mathias, P.M., Beattie, S., Hamilton, H., Morain, C.O., *Effects of vitamin antioxidant supplementation on cell kinetics of patients with adenomatous polyps*, Nov. 10 1992, Department of Gastroenterology, Meath and Adelaide Hospitals, Trinity College, Dublin, Ireland.

Tannenbaum, S.R., Wishnok, J.S., Leaf, C.D., *Inhibition of nitrosamine formation by ascorbic acid*, American Journal of Clinical Nutrition 1991; 53:247S–50S.

Padh, Ph.D., H., *Vitamin C: Newer Insights into its Biochemical Functions*, Nutrition Reviews/vol. 49, No. 3/Mar. 1991.

Johnston, C.S., Meyer, C.G., Srilakshmi, J.C., *Vitamin C elevates red blood cell glutathione in healthy adults*, American Journal of Nutrition 1993; 58:103–5.

Gregory III, Ph.D., J.F., *Ascorbic Acid Bioavailability in Foods and Supplements*, Nutrition Reviews, vol. 51, No. 10, Oct. 1993, 301–309.

Byers, T., Perry, G., *Dietary Carotenes, Vitamin C, and Vitamin E as Protective Antioxidants in Human Cancers*, Annu. Rev. Nutr. 1992 12:139–59.

Mangels, et al., *The Bioavailability to Humans of Ascorbic Acid from Oranges, Orange Juice and Cooked Broccoli Is Similar to That of Synthetic Ascorbic Acid*, American Institute of Nutrition, pp. 1054–1061 (1993).

Yamamoto, I., Tanaka, M., Muto, N., *Enhancement of In Vitro Antibody Production of Murine Splenocytes by Ascorbic Acid 2–O–a–Glucoside*, International Journal of Immunopharmacology, vol. 15, No. 3, pp. 319–325 (1993).

Schwerdt, P.R., Schwerdt, C.E., *Effect of Ascorbic Acid on Rhinovirus Replication in W1–38 Cells (38724)*, Society for Experimental Biology and Medicine (1975).

Cunningham, et al., *Reduced Mononuclear Leukocyte Ascorbic Acid Content in Adults With Insulin–Dependent Diabetes Mellitus Consuming Adequate Dietary Vitamin C*, Metabolism, vol. 40, No. 2, pp. 146–149 (1991).

(List continued on next page.)

Primary Examiner—John Pak
Attorney, Agent, or Firm—Thorpe, North & Western, L.L.P.

[57] ABSTRACT

A vitamin C supplement comprising ascorbic acid, ascorbyl palmitate, niacinamide ascorbate, calcium ascorbate, magnesium ascorbate, potassium ascorbate, and sodium ascorbate which together can be administered to a human to avoid the transitory initial suppression of human NK cell activity which is present when ascorbic acid alone is administered. Also included is xylitol, lysine acetate, tetrasodium pyrophosphate, ribose, cysteine, and hesperidin which further prolongs the biological activity of ascorbic acid and promotes the uptake of ascorbic acid by human tissue.

34 Claims, 4 Drawing Sheets

OTHER PUBLICATIONS

Gleeson, M., Robertson, J.D., Maughan, R.J., *Influence of exercise on ascorbic acid status in man*, Clinical Science (1987) 73,501–505.

Meydani, S.N., *Dietary Modulation of the Immune Response in the Aged*, Human Nutrition Research Center on Aging at Tufts University, Age, vol. 14, 108–115 (1991).

Levine, M.D., M.L., *New Concepts in the Biology and Biochemistry of Ascorbic Acid* The New England Journal of Medicine Apr. 3, 1986.

Harakeh, S., Jariwalla, R.J., Pauling, L., *Suppression of human immunodeficiency virus replication by ascorbate in chronically and acutely infected cells*, Proc. National Academy of Science, USA, vol. 87, pp. 7245–7749, Sep. 1990, Medical Sciences.

Siegel, B.V., Morton, J.I., *Vitamin C and Immunity: Natural Killer (NK) Cell Factor*, Internat. J. Vit. Nutr. Res. 53 1983) 179–183.

Steinbrook, R., *Study Finds Vitamin C Prolongs Life*, New York Times, May 8, 1992.

Lotzova, E., Savary, C.A., Herberman, R.B., *Induction of NK Cell Activity Against Fresh Human Leukemia in Culture with Interleukin*, The Journal of Immunology, vol. 138, 2718–2727, No. 8, Apr. 15, 1987.

Wilson, C.W.M. Vitamin C: Tissue metabolism, oversaturation, Desaturation, and Compensation. University of Ireland, Dublin, Ireland, 1974, pp. 203–220.

Hunt, A.H., "The Role of Vitamin C in Wound healing," The British Journal of Surgery, 1941, pp. 436–461.

Tolbert, B.M., "Metabolism and Function of Ascorbic acid and Its metabolites," Dept. of Chemistry, University of Colorado, Boulder, Colorado, 1985, pp. 121–137.

Schectman, G., "Estimating Ascorbic acid requirements for cigarette Smokers," Annals New York Academy of Sciences, 1993, pp. 335–346.

Inagaki et al., "Studies on the metabolism of fatty acid esters of L–Ascorbic Acid" vitamins, vol. 37, No. 2, 1968, 152–158.

Biological Abstracts 84(9): 90305; abstracting Bush et al., "An Acute study on the relative Gastro–intestinal absorption of novel form of calcium ascorbate" Res. Commun. Chem. Pathol. Pharmacol., vol. 57(1), 1987, pp. 137–140.

Remington's Pharmaceutical Sciences, Mack Publishing Co., Easton, PA, 1990, pp. 1005, 1012–1013, 1021–1022 and 1026–1029.

Baader, S.L. et al., "Uptake and Cytotoxicity of Ascorbic acid . . . " Anticancer Research, vol. 14(1A), Feb. 1994, pp. 221–228.

ASCORBIC ACID COMPOSITIONS PROVIDING ENHANCED HUMAN IMMUNE SYSTEM ACTIVITY

BACKGROUND

1. The Field of the Invention

The present invention relates to dietary supplements and more particularly to dietary supplements providing ascorbic acid.

2. Background of the Invention

It is well-known that vitamin C is necessary for general well being and good health in humans. Because humans are one of the few animals which lack the biochemical mechanisms to synthesize vitamin C, it must be supplied in the diet in the form of food or supplement. Englard, S. and Steifter, S. "The Biochemical functions of Ascorbic Acid," *Ann. Rev. Nutr.* 1986; 365–406. Deficiencies of vitamin C lead to many health complications, such as (a) abnormal bleeding in the skin, mucous membranes, internal organs, and muscles, due to impaired capillary integrity with subcutaneous hemorrhages, (b) edema, (c) joint pain, (d) anorexia, (e) anemias, (f) impaired wound healing, as well as resulting in generally poor health. See Mahan, L. K. and Arlin, M. T. 1992, KRAUSES'S FOOD, NUTRITION AND DIET THERAPY 8th ed. Philadelphia, W. B. Sauders; Anderson, W. A. D., 1971 and PATHOLOGY 6th ed. St. Louis, The C. V. Mosby Company.

Vitamin C deficiencies in children can result in joint swelling, arrested skeletal development, tenderness and swelling of joints, impaired wound healing, anemia and inadequate tooth development. See Anderson, W. A. D., 1971. PATHOLOGY 6th ed. St. Louis: The C. V. Mosby Company. Diseases like scurvy, which is characterized by sore and spongy gums, can be prevented with vitamin C supplementation. Except where inborn errors of metabolism such as cystinuria, oxalosis, and hyperuricemia are present, it is accepted wisdom that vitamin C can be taken in megadoses without toxic side effects. See Stanbury, J. B., Wyngaarden, J. B., Fredrickson, D. S., 1972, THE METABOLIC BASIS OF INHERITED DISEASE 3rd ed. McGraw Hill.

Vitamin C has many different mechanisms by which it offers a protective and beneficial effect. See Anderson, R., 1981 ASCORBIC ACID AND IMMUNE FUNCTIONS: MECHANISM OF IMMUNOSTIMULATION IN VITAMIN C (ASCORBIC ACID) ed. by Counsell, J. N. and Hornig, D. H. 249–272, New Jersey, Applied Science Publishers; Block, G. "Vitamin C and Cancer Prevention: The Epidemiologic Evidence" *Am. J. Clin. Nutr.* 1991, 53:270S-82S; Linder, M. C. 1991 NUTRITIONAL BIOCHEMISTRY AND METABOLISM WITH CLINICAL APPLICATIONS 2d ed. New York, Elsever.

Clinical evidence has demonstrated that ascorbic acid participates in the hydroxylation reactions associated with cholesterol metabolism. Ginter, E. "Cholesterol: Vitamin C Controls Its Transformation to Bile Acids" *Science* 1973, 179:702–704. Cholesterol is produced in the body by certain organ metabolism, as well as being acquired by dietary intake. The human body rids itself of excess cholesterol either in its unchanged form, excreted as waste, or through a series of reactions by which the cholesterol is transformed into bile acids in the liver and later excreted as waste. Studies have shown that a deficiency in ascorbic acid in guinea pigs results in an accumulation of cholesterol in the blood plasma. Id. It has been theorized that with a low concentration of vitamin C, cholesterol cannot be converted into bile acids in the liver. The accumulation of cholesterol in blood plasma can lead to undesirable atheromatous changes in the blood vessels.

Another matter related to metabolism of cholesterol and vitamin C deficiency involves the cytochrome P-450 and cytochrome P-450 reductase. Id. These cytochromes are involved with the C7-hydroxylation of cholesterol. Both the levels of cytochrome P-450 and cytochrome B in the liver decreases 24 hours after depletion of vitamin C from the diet. A low count of cytochrome P-450 is a very sensitive indicator of early scurvy.

Another beneficial effect of vitamin C is the elevation of glutathione, a component of red blood cells. Glutathione is an important antioxidant defense mechanism. Reduced glutathione promotes the antioxidant properties of vitamin C and E. Low plasma levels of reduced glutathione is associated with depressed immunity. Studies have shown that vitamin C supplementation (e.g., 500 mg/day) increases plasma concentrations of glutathione. Johnston, C. S. et al. "Vitamin C Elevates Red Blood Cell Glutathione in Healthy Adults" *Am. J. Clin. Nutr.* 1993, 58:103–105.

It has also been postulated that vitamin C has highly important functions in some hydroxylation reactions. Englard, S. and Steifter, S. "The Biochemical functions of Ascorbic Acid," Ann. Rev. Nutr 1986, 6:365–406 Such reactions include those important to human well being including the formation of epinephrine from DOPA and the hydroxylation of aromatic compounds in the liver.

Further beneficial effects of vitamin C have been recognized in studies on fibroblast cell cultures which indicate that the hydroxylation reaction of proline and lysine in protocollagen occurs in the presence of ascorbic acid. Id. Without ascorbic acid, collagen forms abnormally and becomes weak, which increases the chance of hemorrhaging and slow healing. The enzyme hydroxylase which forms the bonds between proline and hydroxylysine of collagen requires oxygen, a ferrous ion, and a reductant. While ascorbic acid is not the only reductant used for the formation of the collagen bonds between proline and hydroxylysine, it is, however, the most effective compound for the reaction.

It is well-known that smoking is a great hazard to a person's health because it causes a wide variety of metabolic changes. In the case of vitamin C, smoking lowers the vitamin C levels in blood plasma. It is believed that the nicotine in smoke releases catecholamine from the adrenal glands in their active circulation form. When the compounds are in their active form, their biosynthesis consumes ascorbic acid.

Perhaps most notable of the beneficial effects of vitamin C is the large role it plays in supporting the function of the human immune system. As a therapeutic agent, ascorbic acid has been shown to be useful for certain types of cancer treatments. Indeed, there is consistent epidemiological evidence that supports the concept that ascorbic acid provides a protective effect from a variety of human and animal tumors. Vitamin C is postulated to stimulate the human immune system by enhancing interferon synthesis and lymphocyte activity, particularly the class of lymphocyte referred to as natural killer (NK) cells. Sigel, B. V. & Morton, J. I. "Vitamin C and Immunity: Natural Killer (NK) cell factor" *Int. J. Vitamin & Nutrition Res.* 1983, 53:179–183; Lovzova, E., Savary, C. A., & Heberman, R. B. "Induction of NK cells activity against fresh human leukemia in culture with interlukin 2" *J. Immunology* 1987, 138:2718–2727. Natural killer cells are lymphocytes that spontaneously kill tumor or virus-infected cells. Decreased numbers of circulating NK cells have been linked to the development and progression of various immunodeficiencies, viral infections, AIDS, and cancer.

Moreover, vitamin C is believed to provide further benefits by acting as an antioxidant aiding the immune system by reducing the amount of free radical damage that can occur as a result of normal body metabolism as well as from exogenous sources (e.g., pollution). Free radicals have been shown to play a role in tumorigenesis by causing lipid peroxidation and damage to DNA.

BRIEF SUMMARY AND OBJECTS OF THE INVENTION

In view of the above described state of the art, the present invention seeks to realize the following objects and advantages.

It is a primary object of the present invention to provide an improved vitamin C composition and method of administering vitamin C to humans.

It is also an object of the present invention to provide more rapid uptake and utilization of ascorbic acid by humans.

It is another object of the present invention to provide a composition including ascorbic acid which provides more desirable overall effect on the human immune system than that provided by ascorbic acid alone.

It is another object of the present invention to provide a vitamin C composition and a method of administering the same which enhances the activity of human natural killer immune cells.

It is a further object of the present invention to provide a vitamin C composition and method of administering the same which provides prolonged beneficial effects.

It is yet another object of the present invention to provide a composition and method of administering the same which provides better uptake of ascorbic acid by human tissue.

These and other objects and advantages of the invention will become more fully apparent from the description and claims which follow, or may be learned by the practice of the invention.

The present invention provides a dietary vitamin C composition which supplies essential ascorbic acid while enhancing human natural killer (NK) immune cell cytotoxic activity. In comparison, administration of ascorbic acid alone causes a transient suppression or inhibition of NK cell activity shortly after administration. Desirably, administration of preferred formulations of the present invention does not cause any substantial suppression of NK cell activity. Some preferred formulations of the present invention also result in increased uptake of ascorbic acid into peripheral blood leukocytes with peak uptake of the present invention being up to about 18–25 percent better than when ascorbic acid alone is administered.

The present invention provides necessary ascorbic acid in a variety of formulations. The preferred formulations of the present invention include at least at least one water soluble form of ascorbic acid which is biologically acceptable for consumption by humans and at least one fat soluble ascorbyl ester. The water soluble form of ascorbic acid and the fat soluble ascorbyl ester are present in a ratio of between about fifty to one (50:1) and about five to one (5:1) with ratios of between about forty to one (40:1) and about ten to one (10:1) being preferred and a ratios of between about thirty seven to one (37:1) and twenty five to one (25:1) being most preferred. The water soluble form of ascorbic acid and the fat soluble ascorbyl ester are present in a form which can be therapeutically administered to a human.

The water soluble form of ascorbic acid can be selected from the group consisting of ascorbic acid, a biologically acceptable mono or divalent metal ion salt of ascorbic acid and niacinamide ascorbate, and mixtures thereof. Suitable metal ion salts of ascorbic acid are those selected from the group consisting of: calcium ascorbate; magnesium ascorbate; potassium ascorbate; and sodium ascorbate, either alone or some mixture thereof. Other water soluble forms can include: manganese ascorbate; zinc ascorbate; iron ascorbate; copper ascorbate; boron ascorbate; molybdenum ascorbate; and chromium ascorbate.

The fat soluble ascorbyl esters preferably comprise fatty acid esters of $C_1$ to $C_{20}$ saturated or unsaturated carboxylic acids with esters of $C_{10}$ to $C_{20}$ carboxylic acids being preferred and with ascorbyl palmitate being particularly preferred. Other fat soluble esters of ascorbic acid which are preferred include: ascorbyl palmitate; ascorbyl arachidonate; ascorbyl stearate; ascorbyl linoleate; ascorbyl linoleneate; ascorbyl oleate. Ascorbyl acetate and ascorbyl butyrate, while less preferred, are also suitable. The inclusion of fat soluble ascorbyl esters increases the penetration of ascorbic acid across the bilayer lipid membranes in human tissue. When other fat soluble esters of ascorbic acid are used they should preferably be present in an amount so that the total weight concentration of ascorbate contributed by all ascorbyl esters is from about 1% and about 2% and the total ascorbyl content is between about 1.5 and about 5%.

The formulations of the present invention can also preferably include therapeutically beneficial amounts of one or more ascorbic acid metabolites which positively affect or enhance NK cell activity when administered concurrently with water soluble forms of ascorbic acid and a fat soluble ascorbyl ester. The metabolites are most preferably members selected from the group consisting of: basic amino acids; metabolic by-products of ascorbic acid breakdown; flavonoid; sulfur containing amino acids; tetrasodium pyrophosphate; and glutathione, each of which provides one or more beneficial results. Specific preferred metabolites within the above groups can be selected from the group consisting of: 1-lysine acetate; arginine; histidine; xylitol; 1-xylonic acid; 1-lyxonic acid; 2,3 diketo-1-gulonic acid; hesperidin; rutin; proanthocyanidins; methoxyflavonols; alpha-d-ribofuranose; 1-cysteine; cystine; and methionine. The weight ratio of the combined forms of water and fat soluble ascorbic acid derivatives to metabolites may vary within wide ranges, generally from about 1000:1 to 2:1.

DETAILED DESCRIPTION OF THE PREFERRED EMBODIMENTS

While the administration of ascorbic acid provides substantial benefits to humans, the present invention recognizes that administration of ascorbic acid alone does have a significant drawback. Importantly, the administration of ascorbic acid as a dietary supplement causes an undesirable temporary suppression of human immune activity shortly after administration of ascorbic acid and before the beneficial effect of enhancing the human immune response is realized.

It has been shown that both ascorbic acid and vitamin C metabolites enhance NK cell cytotoxic activity. Importantly, when ascorbic acid is administered a biphasic pattern of activity is observed: an early transient suppression or inhibition of NK cell activity occurs, the period of inhibition lasting for about two to four hours, followed by enhancement of NK cell activity.

The inhibition of NK cell activity after administration of ascorbic acid is potentially a serious side effect. The inhibition of NK cell activity, in practice, can have a prolonged effect. For example, the inhibition of NK cell activity may be prolonged if ascorbic acid is administered on a regular basis, e.g., every four hours.

The disadvantageous transient inhibition of NK cell activity is recognized by, as well as avoided by, the present invention as will be explained below. Importantly, the two to four hour transitory inhibition of NK cell activity which is experienced when ascorbic acid alone is administered could allow any existing pathogens to greatly multiply. Because the doubling population rate for certain bacteria is 20 minutes, it is possible that some bacteria could multiply by a factor of 64 during the transitory suppression of NK cell activity.

Importantly, NK cell activity and decreased numbers of circulating NK cells has been linked to the development and progression of many malignant diseases such as cancer, chronic and acute viral infections, chronic fatigue syndrome, psychological dysfunction, and certain autoimmune diseases (including AIDS). Evidence shows that ascorbic acid and vitamin C metabolites may be helpful in reversing NK cell deficiencies. Because NK cells have the ability to mediate natural resistance against tumors, factors that enhance or influence NK cell activity, such as ascorbic acid, may be applied to treatment or prevention against such malignancies.

The anticancer activity of ascorbic acid has been the subject of studies. Some of such studies show that ascorbic acid causes regression of skin tumors and estrogen-induced renal tumors in vivo. Other studies suggest that ascorbic acid demonstrates antitumor activity against breast and gastric cancer.

Ascorbic acid possesses potent immunomodulator properties and its property of enhancing natural killer cell activity should be exploited to maximize its anti-cancer and anti-tumor activity. The present invention maximizes the benefits of ascorbic acid while avoiding the serious disadvantage of the transitory suppression of NK cell activity. Moreover, the present invention also enhances other benefits of ascorbic acid as will be explained below.

As explained earlier, humans must ingest some form of ascorbic acid to maintain health and well being. The formulations of the present invention described herein provide the necessary ascorbic acid accompanied by beneficial effects not before available in the art.

The present invention is an ascorbic acid composition, which can be administered orally or otherwise, for use as a dietary supplement. The formulations of the present invention function as a nutritional supplement, antioxidant, and/or an immune system modulator.

The present invention provides a composition containing bioavailable ascorbic acid in both water and fat soluble forms. This composition is also preferably accompanied by other ascorbic acid metabolites which sustain, prolong and/or enhance the therapeutic properties of ascorbic acid. The preferred formulations of the present invention include at least at least one water soluble form of ascorbic acid which is biologically acceptable for consumption by humans and at least one fat soluble ascorbyl ester.

Water Soluble Forms of Ascorbic Acid.

It is to be understood that the term ascorbic acid is intended to refer to ascorbic acid, and any of its biologically active equivalents or alternative labels by which it is known including, for example, vitamin C, 1-ascorbic acid, 1-xyloascorbic acid, 3-oxo-1-gulofuranolactone, 1–3-ketothreohexuronic acid, antiscorbutic vitamin, cevitamic acid, and various trade names.

The water soluble form of ascorbic acid can be a member selected from the group consisting of ascorbic acid, a biologically acceptable mono or divalent metal ion salt of ascorbic acid and niacinamide ascorbate. The mono or divalent metal ion salts of ascorbic acid are preferably selected from the group consisting of calcium ascorbate, magnesium ascorbate, potassium ascorbate, and sodium ascorbate. Other water soluble forms of ascorbic acid can also be included as shown in Table B, below.

Preferred formulations are those which contain a combination of calcium and magnesium ascorbate and sodium and potassium ascorbate. This combination of alkaline earth and alkali metal ascorbates appear to complement each other as the preferred core grouping of water soluble ascorbates.

Niacinamide ascorbate is also desirable in that it provides ascorbate to the tissues and provides a non-histamine producing form of vitamin $B_3$. Niacinamide ascorbate also improves the tableting characteristics of the formulations of the present invention.

In many instances it is also desirable to have a certain amount of ascorbic acid present as part of the water soluble ascorbic acid mixture.

In the most preferred formulations, the weight ratio of all water soluble forms of mineral salts of ascorbic acid and niacinascorbate to ascorbic acid is between about 10:1 and about 5:1, with a ratio of about 7.5:1 being the most preferred ratio. The preferred ratio of sodium ascorbate to potassium ascorbate is between about 6:1 and about 4:1, with about 4.4:1 being most preferred. The preferred ratio of calcium ascorbate to magnesium ascorbate is between about 10:1 and about 5:1, with about 7.5:1 being most preferred.

Fat Soluble Forms of Ascorbic Acid (Ascorbyl Esters).

The fat soluble ascorbyl esters preferably comprise fatty acid esters of $C_1$ to $C_{20}$ saturated or unsaturated carboxylic acids with esters of $C_{10}$ to $C_{20}$ carboxylic acids being preferred. Representative of the broad scope of $C_{10}$ to $C_{20}$ ascorbyl esters which may be utilized are the members selected from the group consisting of ascorbyl palmitate, ascorbyl arachidonate, ascorbyl stearate, ascorbyl linoleate, ascorbyl linoleneate, and ascorbyl oleate and mixtures thereof. Representative of the less preferred $C_1$ to $C_9$ ascorbyl esters are, ascorbyl acetate, ascorbyl butyrate, and mixtures thereof. Ascorbyl palmitate is particularly preferred. The inclusion of fat soluble ascorbyl esters increases the penetration of ascorbic acid across the bilayer lipid membranes in human tissue.

The water soluble form of ascorbic acid and the fat soluble ascorbyl ester are present in a ratio of between about fifty to one (50:1) and about five to one (5:1) with ratios of between about forty to one (40:1) and about ten to one (10:1) being preferred and ratio of between about thirty seven to one (37:1) and twenty five to one (25:1) being most preferred. The water soluble form of ascorbic acid and the fat soluble ascorbyl ester are present in a form which can be therapeutically administered to a human.

Ascorbic Acid Metabolites.

A "metabolite" can be either a substance essential to or affecting metabolism or a product of metabolism. As used herein, the term "metabolite" is intended to be given such broadest meaning.

The formulations of the present invention can also preferably include therapeutically beneficial amounts of one or more ascorbic acid metabolites which positively affect or enhance NK cell activity when administered concurrently with water soluble forms of ascorbic acid and a fat soluble ascorbyl ester. The metabolites are members selected from the group consisting of: basic amino acids; metabolic by-products of ascorbic acid breakdown; flavonoid; sulfur containing amino acids; tetrasodium pyrophosphate; and glutathione, each of which provides one or more beneficial results. Provided below is a list of preferred metabolites which may be used, either alone or in combination, in the formulations of the present invention.

Basic Amino Acids:

Basic or diamino-monocarboxylic acids tend to reduce urinary excretion of ascorbic acid, slow down the breakdown of ascorbic acid in warm-blooded animals and increase total ascorbic acid blood plasma levels. The basic amino acids used are those selected from the group consisting of lysine, arginine, and histidine with lysine being preferable. These can be used in their free base or acid addition salt forms. Lysine acetate has been found particularly useful in the formulations of the present invention.

Amino acids selected from the group consisting of lysine, arginine, histidine and glycine and their acid addition salts are preferably included in the formulations of the present invention because they tend to reduce urinary excretion of, and also slow the breakdown of, ascorbic acid in humans. The basic amino acids, lysine, arginine and histidine, and their salts are preferred with lysine being particularly preferred. Lysine also increases total ascorbic acid blood plasma levels, as well as ascorbic acid levels in the liver, kidney, testicle, spleen, and brain tissue. Most preferably lysine is utilized as lysine acetate.

Metabolic By-products of Ascorbic Acid Breakdown:

There are various metabolic by-products of the pathway of ascorbic acid breakdown or metabolism. The addition of one or more of these to the formulations of the present invention tend to slow the breakdown of ascorbic acid. Representative of such by-products are those selected from the group consisting of xylitol, 1-xylonic acid, 1-lyxonic acid, 2,3 diketo-1-gulonic acid, ribose, α-d-ribofuranose, ribulose and d-ribose-5-phosphoric acid. Of these α-d-ribofuranose and 1-xylonic acid used in combination are most preferred.

Flavonoid:

Flavonoid, or Vitamin P as they are sometimes called, have a constrictor action on the capillary bed and decrease the permeability thereof. Also, flavonoid are thought to have an ascorbic acid sparing action by virtue of their reducing properties. One or more flavonoid selected from the group consisting of hesperidin, rutin, quercetin, proanthocyanidins, flavonols, and methoxyflavonols may preferably be included in the formulations of the present invention. The presence of hesperidin is particularly preferred.

Sulfur Containing Amino Acids:

Sulfur containing amino acids selected from the group consisting of cysteine, cystine, and methionine are preferably included in the formulations of the present invention because of their activity in the control of dehydroascorbatase, the enzyme involved in the catabolism of ascorbic acid. Their presence tends to slow ascorbic acid degradation and thus prolongs desirable blood levels of ascorbic acid. The inclusion of cysteine is preferred in the present formulations.

Tetrasodium pyrophosphate:

Tetrasodium pyrophosphate is preferably included in the present formulations as a metabolite which enhances tissue transport of ascorbic acid and provides a pyrophosphate as an energy source in many biophysical reactions. Tetrasodium pyrophosphate further tends to slow the rate of ascorbic acid degradation in the body.

Glutathione:

Glutathione, in reduced form, is an important antioxidant which supports and enhances the antioxidant properties of Vitamins C and E.

Of the metabolites listed above, set forth below are those which are most preferred and the preferred weight ratio range (shown in parentheses) of the particular metabolite to glutathione (reduced): xylitol (25:1 to 45:1 and most particularly 35:1); l-lysine acetate (7:1 and 13: and most particularly 10.5:1); hesperidin (4:1 and 10:1 and particularly 7:1); α-d-ribofuranose (1.5:1 and 4:1 and particularly 2.8:1); l-cysteine (1:1 to 3:1 and particularly 2:1); tetrasodium pyrophosphate (2:1 and 4:1 and particularly 3:1).

The most presently preferred formulation of the present invention is an admixture of ascorbic acid, ascorbyl palmitate, niacinamide ascorbate, calcium ascorbate, magnesium ascorbate, potassium ascorbate, and sodium ascorbate. The most presently preferred formulation of the present invention also includes xylitol, lysine acetate, tetrasodium pyrophosphate, ribose, cysteine, and hesperidin all of which function as a "precursor supporting system" of metabolites. The components of the precursor supporting system further enhance the beneficial effects of ascorbic acid as will be explained shortly. Furthermore, some components of the precursor supporting system provide a synergistic effect whereby the reactions between vitamin C and other compounds, such as vitamin E, are enhanced.

In the most presently preferred formulation, a dose in accordance with the present invention provides between about 60 mg and about 1500 mg of ascorbic acid derived from the following components: 1-xyloascorbic acid; niacinamide ascorbate; ascorbyl palmitate; calcium ascorbate; magnesium ascorbate; potassium ascorbate; and, sodium ascorbate. Moreover, a dose of the most presently preferred formulation of the present invention also contains the following ascorbic acid precursors: l-lysine acetate; xylitol; hesperidin; alpha-d-ribofuranose; l-cysteine; tetrasodium pyrophosphate; and, glutathione.

Importantly, the ascorbate components of the present invention provide the necessary ascorbic acid but the initial transitory suppression of NK cell activity which occurs when ascorbic acid is administered alone is beneficially avoided with the present invention. In contrast to the present invention, the prior art teaches that a large dose of ascorbic acid alone should be administered accompanied by an undesirable transitory suppression of NK cell activity.

The present invention also functions to enhance a number of additional beneficial effects of ascorbic acid and increases its effectiveness as will be more fully explored below. Administration of formulations of the present invention increases blood plasma levels of ascorbic acid above that experienced when ascorbic acid alone is administered. Administration of formulations of the present invention results in ascorbic acid being absorbed more quickly and retained in the human body longer than when ascorbic acid alone is administered. Moreover, the present invention provides additional benefits such as greater bioactivity, greater penetrability of ascorbic acid across bilayer lipid membranes, delayed oxidation of vitamin E in the human body, providing of pyrophosphates which are used as energy sources for biophysiological reactions in humans, and slowed rate of degradation of ascorbic acid in humans.

As mentioned, the preferred formulation of the present invention includes selected compounds in addition to ascorbic acid. The additional compounds have particular beneficial functions as will now be explained.

A fat soluble $C_1$–$C_{20}$ carboxylic acid ester of ascorbic acid, wherein an —OH from the ascorbic acid functions as an alcohol in the ester formation, is preferably included in the formulations of the present invention because of its fat solubility. The inclusion of ascorbyl fatty acid esters increases the penetration of ascorbic acid across the bilayer lipid membranes in human tissue. The inclusion of ascorbyl esters also delays the oxidation of vitamin E in humans, thereby prolonging the antioxidative effect of vitamin E. The carboxylic acids can be either saturated, unsaturated, including polyunsaturation, e.g., arachidonic acid. Esters of $C_{10}$ to $C_{20}$ carboxylic acids are preferred with esters of $C_{12}$–$C_{18}$ carboxylic acid being particularly preferred. Ascorbyl palmitate is most preferred as the ascorbyl ester.

The formulations of the present invention are preferably provided in tablet form though it will be appreciated that such may also be provided in capsule, gelcap, powder or liquid form. For the desired results, the proper dosages can be from one (1) to ten (10) tablets, each tablet providing from 60 mg to 1500 mg of ascorbic acid, daily.

Provided below are several examples disclosing various formulations which are listed in Table B, set forth below following the examples.

EXAMPLE 1

This example compares the effect of ascorbic acid and the formulation of the present invention on NK cell activity, NK cell population, and peripheral blood leukocyte (PBL) uptake. The formulation of the present invention considered in this example is that which is set forth in Table B as Formulation I.

Twenty-two healthy subjects were randomly selected for this example. The subjects ranged in age from 20 to 24 years, with a mean of 22 years. The subjects had not ingested any medications for at least two weeks before participation in the study.

Eleven of the volunteers were given 60 mg of ascorbic acid per kilogram of body weight, and the remaining eleven were given a biologically equivalent amount of the preferred formulation (Formulation I, Table B) of the present invention per kilogram of body weight. Each subject had 10–15 ml of blood drawn at 0, 1, 2, 4, 6, 8, 24, and 48 hours post administration. Clearance and the uptake of ascorbic acid was measured in the plasma and mononuclear cell, respectively. Additionally, NK cell cytotoxic activity before and after administration were determined.

Preparation of Mononuclear Cells:

Lymphocytes were prepared from fresh heparinized peripheral venous blood by Ficoll-Hypaque density gradient centrifugation (Litton Bionetics, Rockville, Md.). Cells were washed three times with Hanks' balanced salt solution (HBSS), and resuspended to a concentration of $10 \times 10^6$ cells/ml in a complete medium (CM), that consisted of RPMI-1640 supplemented with 10% fetal calf serum and 1% antibiotics (100 U penicillin and 100 μg/ml streptomycin) and within an hour of isolation cells were used for different assays.

Measurement of Vitamin C in Plasma and its uptake by PBL:

Ascorbic acid in plasma or its uptake by peripheral blood lymphocytes was determined according to the spectrophotometric method previously described in Nino, H. V. & Parasad., "Vitamins and trace elements" GRADWOHL'S CLINICAL LABORATORY METHODS AND DIAGNOSIS pp. 370–372 (ed. by Sonnenwirth, A. C. & Jarett, L.) (1980). Briefly described, $5 \times 10^6$ cells were suspended in 0.2 ml of PBS, sonicated for 30 seconds, and 1 ml of 5% trichloroacetic acid (TCA) was added. The mixture was centrifuged to remove the precipitates and the supernatant was used to measure the level of ascorbic acid. From the mixture, 1.2 ml of this supernatant or 0.5 ml plasma was mixed with 0.4 ml of Dinitrophenyl-hydrazine-Thiourea-Copper (DCT) reagent, incubated at 37° C. for 3 hours, then transferred to an ice-water bath for 10 minutes. Then 2 ml of cold 12M $H_2SO_4$ was added and the mixture was kept at room temperature for 20 min. Ascorbic acid was measured in controls (both serum and PBL from the individuals prior to administration of ascorbic acid), and ascorbic acid-treated specimens at 520 nm and results were estimated from a calibration graph.

Chromium-release Assay for measuring NK cell activity:

A standard 4-hr $^{51}$Cr-release assay was employed. Briefly, $1 \times 10^4$ $^{51}$Cr-labelled K562 tumor target cells in 0.1 ml CM were added to different wells of a microtiter plate. Effector cells were then pipetted into quadruplicate wells to give effector: target (E:T) ratios of 6:1, 12:1, 25:1 and 50:1. After a 4-hr incubation at 37° C., the microtiter plates were centrifuged at 1400 rpm for 5 min and 0.1 ml of supernatant from each well was collected and counted in a gamma counter. The percentages of isotope released were calculated by the following formula:

$$\% \text{ Lysis} \frac{\text{ExperimentalRelease} - \text{SpontaneousRelease}}{\text{TotalRelease} - \text{SpontaneousRelease}} \times 100$$

Spontaneous release from the target cells was always no more than 8–10% of total release. Total release was measured by adding 0.1 me Triton X-100 to designated wells. Lytic units (LU) were calculated from effector titration curves. One LU was defined as the number of effector cells required to achieve 20% lysis.

NK Sub-populations:

NK cell subset enumeration was carried out in ascorbate-treated and non-treated cell populations. A single laser flow cytometer (Epics Profile: Coulter Epics, Inc., Hialeah, Fla.), which discriminates forward and right-angle light scatter, as well as two colors, was used with an appropriate software package (Quad Stat: Coulter). Mononuclear cell populations were determined by two-color direct immunofluorescence, by using a whole-blood staining technique with the appropriate monoclonal antibody and flow cytometry. The fluorescein isothiocyanate (FITC), or phycoerythrin (PE)-conjugated monoclonal antibodies (Coulter Immunology) CD56 PE and CD3-FITC were selected for determination of total NK cells and NKHT3$^+$/NKHT3$^-$cells. To monitor lymphocyte markers, bit maps were set on the lymphocyte population of the forward-angle light scatter versus a 90° light scatter histogram. The percentage of positively stained cells for each marker pair, as well as the percentage of doubly stained cells, was determined. Estimates of the absolute numbers of lymphocyte positive for the respective surface markers were determined by multiplying peripheral lymphocyte cell count by the percentage of cells positive for each surface marker.

The effect of administration of ascorbic acid alone and the effect of administration of the formulation of the present invention (Formulation I Table B) are shown in FIGS. 1A–B, 2, and 3.

Figure 1A:
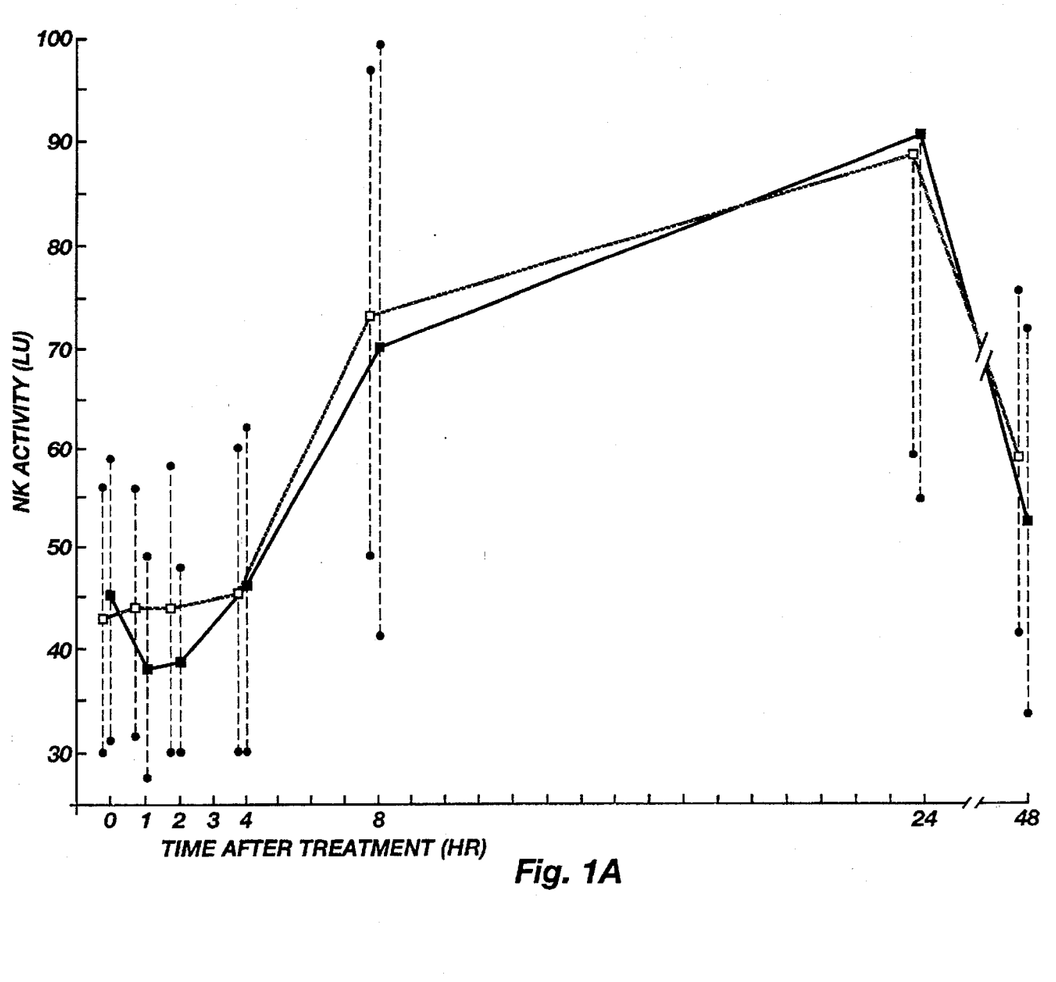
FIG. 1A is a graph showing the enhancement of natural killer cell activity obtained when a formulation of the present invention is used on humans in comparison to when ascorbic acid alone is administered.

FIG. 1A shows the time-course of the changes in NK cell activity in the subjects treated with ascorbic acid alone or the formulation of the present invention. Not represented in FIG. 1A is the control which showed that, without administration of either ascorbic acid alone or a formulation of the present invention, the NK cell activity remained in the range from 42–44 LU.

In FIG. 1A the NK cell activity is represented in lytic units (LU) on the vertical axis with time being represented in hours on the horizontal axis. The solid line and solid boxes plot the results obtained using ascorbic acid alone. The broken line and hollow boxes plot the results obtained using the presently preferred formulation of the present invention.

FIG. 1A shows that when ascorbic acid only is administered a transitory decrease in NK cell activity occurs one to two hours after administration with NK cell activity recovering to pre-administration levels at about four hours post-administration. The NK cell activity then continued to increase to 90 LU at twenty-four hours, then declined to near pre-administration levels at forty-eight hours. As explained earlier, the rise in NK cell activity has been previously noted in the art, yet the transitory suppression of NK cell activity shown for about the first four hours post-administration has not been recognized. The vertical dashed lines extending from the blocks indicate the highest and lowest values obtained from various subjects.

Critically, FIG. 1A shows that substantially no suppression of NK cell activity occurs from zero to four hours post-administration of the presently preferred formulation of the present invention (plotted by the broken line and hollow boxes). The avoidance of the transient suppression of NK cell activity experienced when ascorbic acid alone is administered (plotted by the solid line and boxes) is very desirable and a great advance in the art which has heretofore not been recognized in the art.

Figure 1B:
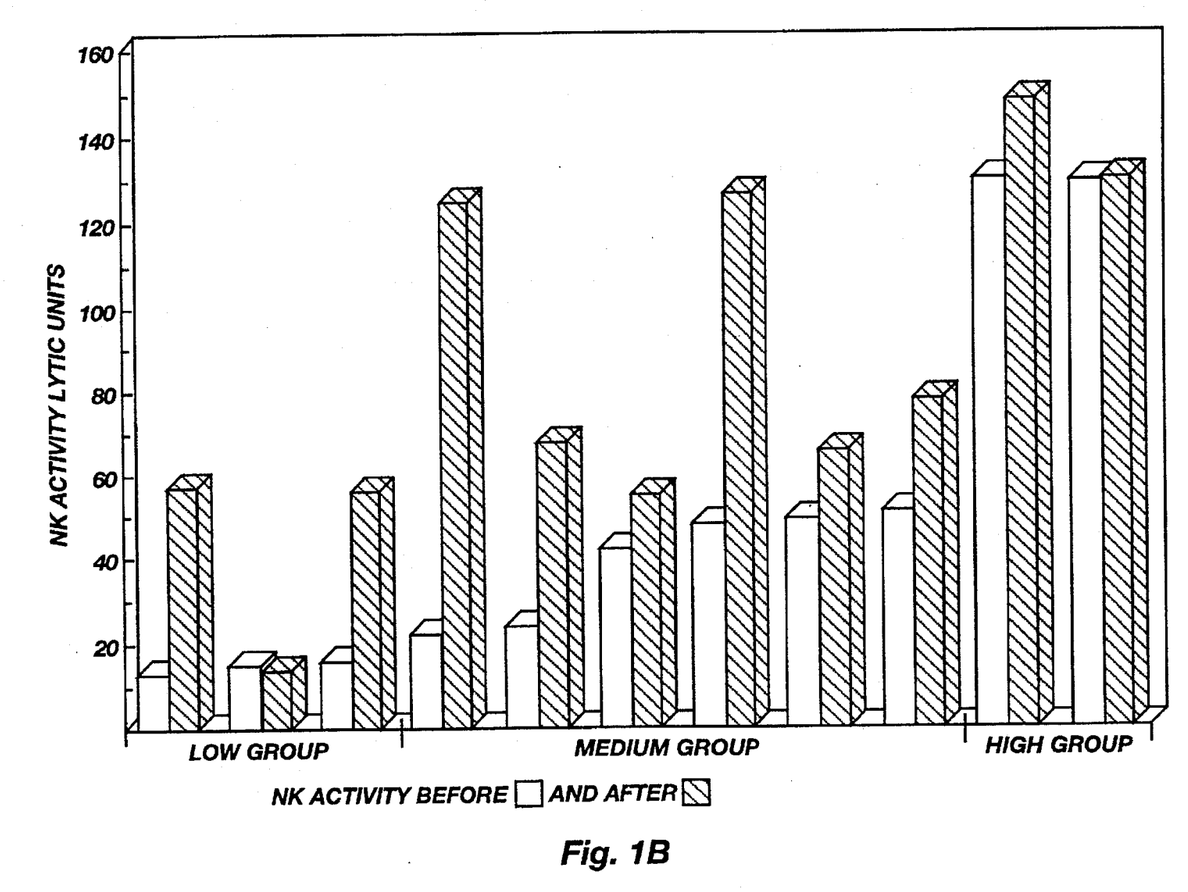
FIG. 1B is a chart showing the enhancement of natural killer cell activity obtained when a formulation of the present invention is used on humans.

FIG. 1B shows that basal NK cell activity, also referred to as cytotoxicity, expressed as number of lytic units (LU) varied widely among the subjects of this example. FIG. 1B shows the lytic units on the vertical axis with the NK cell activity of individual subjects represented by the vertical bars.

FIG. 1B shows that the subjects of this example were divided into three categories: a low category exhibiting between about 10–20 LU and including 5 out of 22 subjects; a medium category exhibiting between about 21–60 LU and including 13 out of 22 subjects; and a high category exhibiting greater than 60 LU and including 4 out of 22 subjects. In FIG. 1B, the hollow bars represent the subject's NK cell activity before administration of either ascorbic acid alone or the formulation of the present invention. The solid bars represent the subject's NK cell activity after administration of the formulation of the present invention.

FIG. 1B shows that nearly every subject showed an increase in NK cell activity upon administration of the formulation of the present invention. The subjects in the medium category experienced the greatest overall increase in NK cell activity upon administration of the formulation of the present invention.

Total NK cell population and its sub-populations were also examined in this example. The total NK cell population and its sub-populations were determined both post-treatment with ascorbic acid alone and post-treatment with the formulation of the present invention by flow cytometry, using Anti-CD56 and Anti-CD3 monoclonal antibodies, respectively. The results of this example show that administration of either ascorbic acid alone or administration of the formulation of the present invention had no significant effect on the percentages of total NK cell population, or its sub-populations, examined at 0 and 24 hours post treatment. In this example, no correlation between percent NK cell and NK cytotoxic activity was demonstrated, some with high percentage had high NK activity and others with low NK percentage had high activity.

Figure 2:
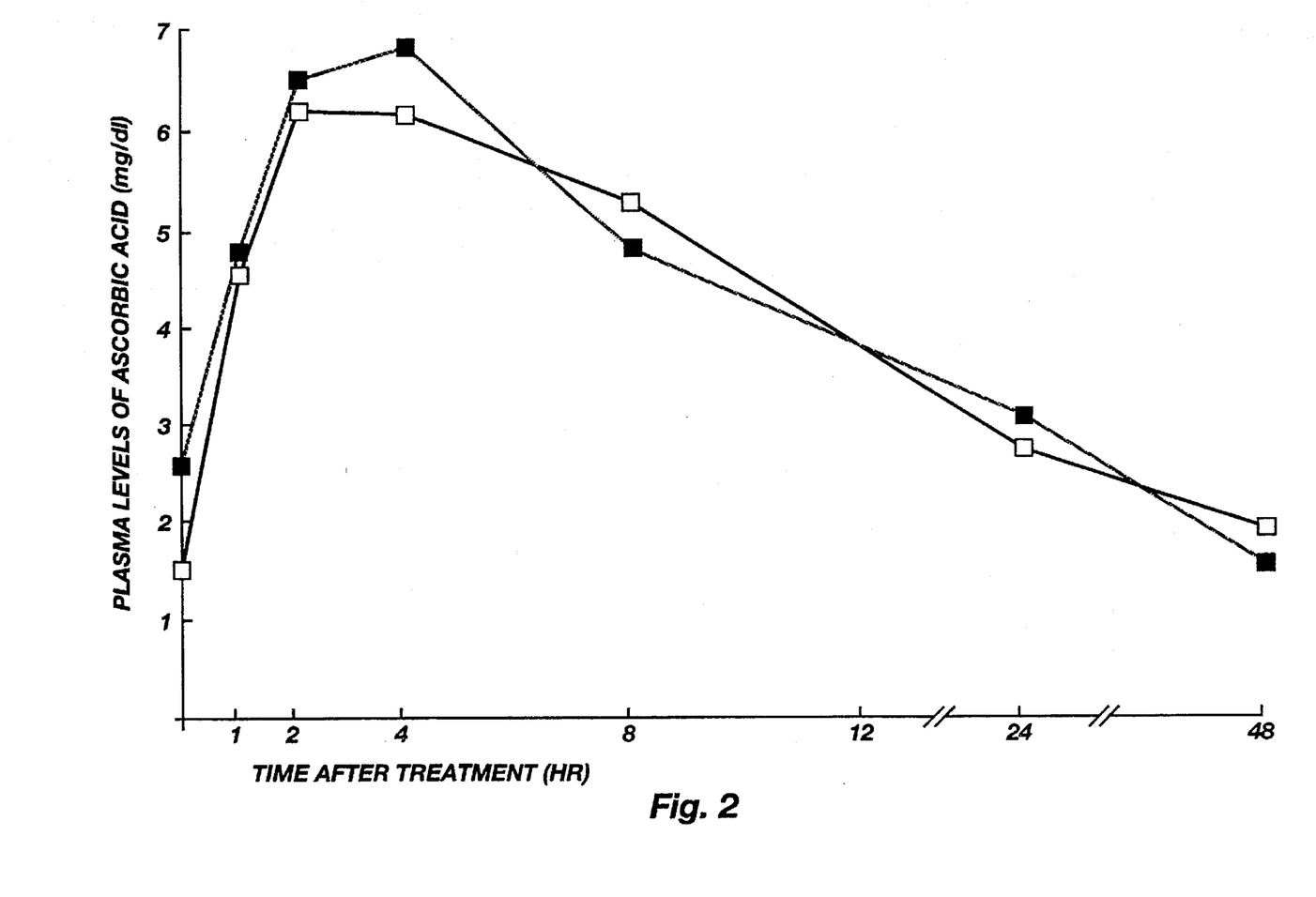
FIG. 2 is a graph comparing the plasma level of ascorbic acid present in humans after administration of a formulation of the present invention and administration of ascorbic acid alone.

This example also demonstrates the additional beneficial effects of the present invention. FIG. 2 shows the increase in blood plasma levels of ascorbic acid after administration of the formulation of the present invention (represented by the broken line and solid boxes) and after administration of ascorbic acid alone (represented by the solid line and hollow boxes). In FIG. 2 the vertical axis represents the level of ascorbic acid in plasma measured in mg/dl and the horizontal axis represents the time after administration, from zero to forty-eight hours.

FIG. 2 shows that the mean level of ascorbic acid before treatment was markedly increased (about 4.2 mg/dl) at 1 hour in both cases. Administration of the presently preferred formulation (Formulation I Table B) provided a slightly higher maximum mean level of ascorbic acid in plasma at about two to four hours after administration (about 6.5 mg/dl) with the level of ascorbic acid in plasma gradually decreasing to about 3.8 mg/dl at 24 hours after administration with plasma ascorbic acid levels returning to pre-administration levels after about forty-eight hours. Advantageously, the presently preferred formulation of the present invention provides plasma levels of ascorbic acid substantially better than, in many instances, than that obtained with ascorbic acid alone.

Figure 3:
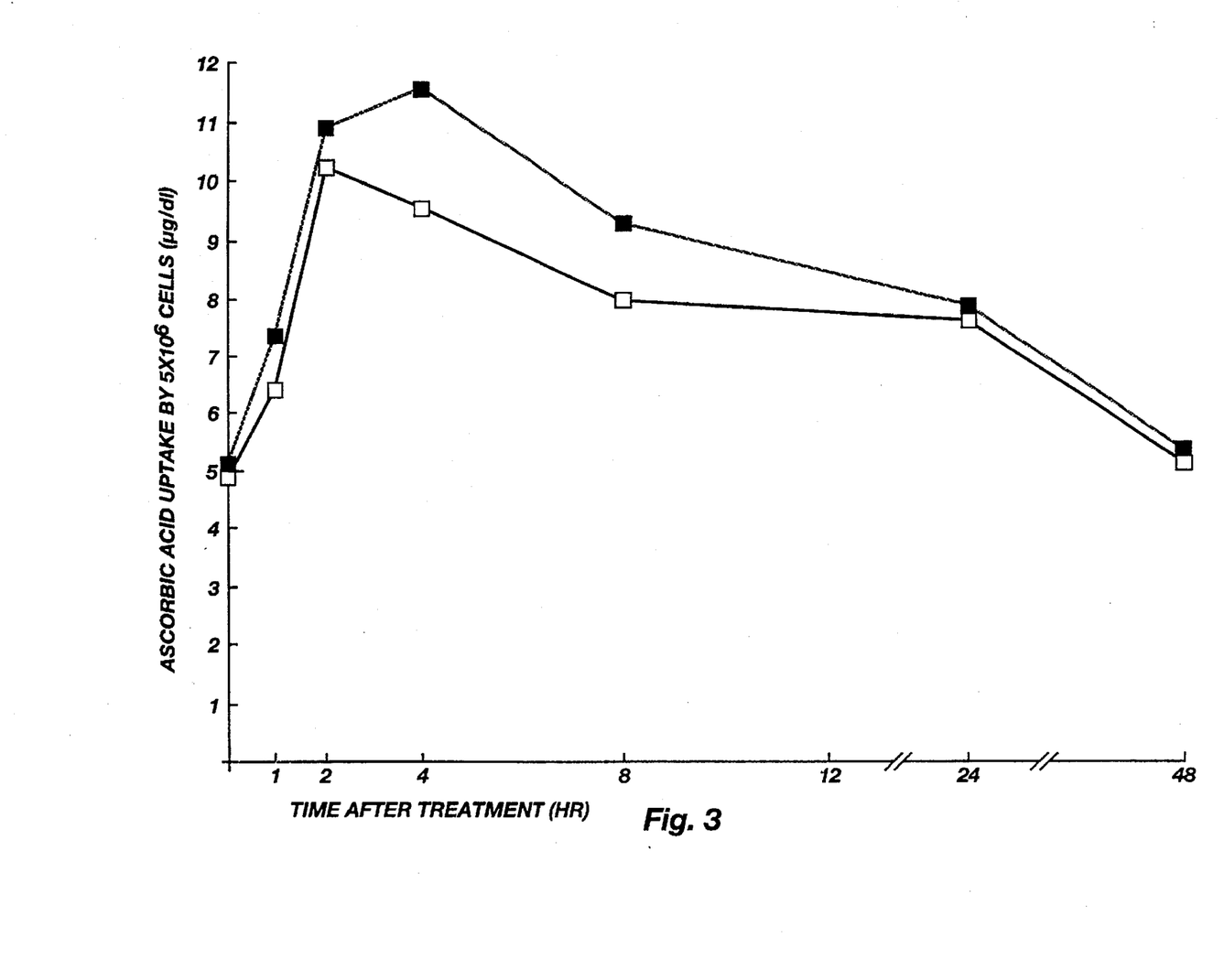
FIG. 3 is a graph comparing the ascorbic acid uptake by human cells after administration of a formulation of the present invention and administration of ascorbic acid alone.

FIG. 3 shows the uptake of ascorbic acid per $5 \times 10^6$ WBC after administration of the formulation of the present invention (represented by the broken line and solid boxes) and after administration of ascorbic acid alone (represented by the solid line and hollow boxes). In FIG. 3, the vertical axis represents the level of ascorbic acid uptake in cells measured in µg/dl and the horizontal axis represents the time after administration, from zero to forty-eight hours.

FIG. 3 shows that the uptake of ascorbic acid measured per $5 \times 10^6$ WBC two hours after administration was higher than the uptake when ascorbic acid alone was administered and remained significantly higher for about twenty-four hours after administration. Overall, administration of the presently preferred formulation of the present invention resulted in ascorbic acid being transported into the cells about 18–25% better than with ascorbic acid alone (P<0.01). Table A provides further data regarding the mean (M±SD) uptake of ascorbic acid by $5 \times 10^6$ white blood cells expressed in µg/dl in accordance with this example.

TABLE A

| | Hours | | | | | | |
| --- | --- | --- | --- | --- | --- | --- | --- |
| | 0 | 1 | 2 | 4 | 8 | 24 | 48 |
| Ascorbic acid alone | 5.1 ±1.2 | 6.4 ±1.3 | 10.1 ±2.1 | 9.5 ±1.9 | 7.9 ±1.9 | 7.4 ±1.7 | 4.9 ±1.1 |
| Formulation I | 5.0 ±1.1 | 7.3 ±1.4 | 10.9 ±3.1 | 11.9 ±3.1 | 9.2 ±2.1 | 7.5 ±1.8 | 5.1 ±1.4 |

EXAMPLE 2

This example compares the effect of ascorbic acid alone and the presently preferred formulation of the present invention on NK cell activity when taken every four hours. Sixteen healthy adult volunteers are randomly selected and for a period of twenty-four hours, eight of the volunteers are given 15 mg of ascorbic acid per kilogram of body weight every four hours and the remaining eight are given a biologically equivalent amount of a formulation of the present invention per kilogram of body weight every four hours. Blood samples are collected at 4, 8 12, 16, 20, and 24 hours and are analyzed for NK cell activity as explained in connection with Example 1. The results of this example show a repeated suppression of NK cell activity in the subjects which received ascorbic acid alone while the subjects which receive the presently preferred formulation of the present invention show continued enhancement of NK cell activity without any suppression.

EXAMPLE 3

This example examines the effect of the presently preferred formulation of the present invention on red blood cell glutathione levels. Reduced glutathione protects cellular constituents from oxidative damage in addition to promoting the antioxidant properties of ascorbic acid and vitamin E. Twelve healthy adult volunteers are randomly selected for this example. The subjects maintain their usual dietary patterns while limiting their intake of ascorbic acid rich foods to one serving or less per day. Under double-blind conditions, subjects ingest a placebo tablet daily during week 1 for baseline readings. During weeks two and three, subjects ingest 250 mg of the presently preferred formulation of the present invention twice daily, and during week four, the subjects ingest four tablets of placebo daily. The placebo and the present invention formulation tablets are identical in appearance. The subjects complete daily dietary records throughout the study of this example. Comparing to baseline values, plasma ascorbic acid levels rise significantly after the second week of supplementation. Mean levels of red blood cell glutathione also rise significantly during this period.

EXAMPLE 4

This example shows the effect of administering a formulation of the present invention on NK cell activity. The formulation in this example is that which is set forth in Table B as Formulation II. Healthy subjects are randomly selected for this example and half of the subjects are given Formulation II while the other subjects were given a biologically equivalent amount of ascorbic acid alone. The results of this example show that administration of the Formulation II causes substantially no suppression of NK cell activity from zero to four hours post-administration of Formulation II. The avoidance of the transient suppression of NK cell activity is very desirable.

EXAMPLE 5

This example shows the effect of administering a formulation of the present invention on ascorbic acid plasma and cell uptake levels as well as on NK cell activity. The formulation in this example is that which is set forth in Table B as Formulation III. Healthy subjects are randomly selected for this example and half of the subjects are given Formulation III while the other subjects were given a biologically equivalent amount of ascorbic acid alone. The results of this example show that administration of the Formulation III provides increased ascorbic acid levels in plasma and white blood cells over the ascorbic acid levels resulting in plasma and white blood cells when ascorbic acid alone is administered. The administration of Formulation III causes substantially the same suppression of NK cell activity from zero to four hours post-administration as results from the administration of ascorbic acid alone.

EXAMPLE 6

This example shows the effect of administering a formulation of the present invention on NK cell activity and ascorbic acid levels in both plasma and cells. The formulation in this example is that which is set forth in table B as Formulation IV. Healthy subjects are randomly selected for this example and half of the subjects are Formulation IV while the other subjects are given a biologically equivalent amount of ascorbic acid alone. The results of this example show that administration of Formulation IV causes an increase in NK cell activity with substantially no suppression of NK cell activity from zero to four hours post-administration of Formulation IV. The avoidance of the transient suppression of NK cell activity is very desirable.

EXAMPLE 7

This example shows the effect of administering a formulation of the present invention on NK cell activity and ascorbic acid levels in both plasma and cells. The formulation in this example is that which is set forth in Table B as Formulation V. Healthy subjects are randomly selected for this example and half of the subjects are given Formulation V while the other subjects are given a biologically equivalent amount of ascorbic acid alone. The results of this example show that administration of Formulation V provides increased ascorbic acid levels in plasma and white blood cells over the ascorbic acid levels resulting in plasma and white blood cells when ascorbic acid alone is administered. The results of this example also show that administration of Formulation V causes an increase in NK cell activity with substantially no suppression of NK cell activity from zero to four hours post-administration of Formulation V. The avoidance of the transient suppression of NK cell activity is very desirable.

EXAMPLE 8

This example shows the effect of administering a formulation of the present invention on NK cell activity. The formulation in this example is that which is set forth in Table B as Formulation VI. Healthy subjects are randomly selected for this example and half of the subjects are given Formulation VI while the other subjects are given a biologically equivalent amount of ascorbic acid alone. The results of this example show that administration of Formulation VI causes substantially the same suppression of NK cell activity from zero to four hours post-administration as results from the administration of ascorbic acid alone.

EXAMPLE 9

This example shows the effect of administering a formulation of the present invention on NK cell activity. The formulation in this example is that which is set forth in Table B as Formulation VII. Healthy subjects are randomly selected for this example and half of the subjects are given 180 mg of Formulation VII per kilogram of body weight while the other subjects are given ascorbic acid alone. The results of this example show that the administration of Formulation VII causes substantially the same suppression of NK cell activity from zero to four hours post-administration as results from the administration of ascorbic acid alone.

EXAMPLE 10

This example shows the effect of administering a formulation of the present invention on NK cell activity. The formulation in this example is that which is set forth in Table B as Formulation VIII. Healthy subjects are randomly selected for this example and half of the subjects are given 180 mg of Formulation VIII per kilogram of body weight while the other subjects are given ascorbic acid alone. The results of this example also show that administration of Formulation VIII causes an increase in NK cell activity with substantially less suppression of NK cell activity from zero to four hours post-administration of Formulation VIII than occurs if ascorbic acid alone is administered. The avoidance of the transient suppression of NK cell activity is very desirable.

EXAMPLE 11

This example shows the effect of administering a formulation of the present invention on NK cell activity and on ascorbic acid levels in both plasma and cells. The formulation in this example is that which is set forth in Table B as Formulation IX. Healthy subjects are randomly selected for this example and half of the subjects are given Formulation IX while the other subjects are given a biologically equivalent amount of ascorbic acid alone. The results of this example show that administration of Formulation IX provides increased ascorbic acid levels in plasma and white blood cells over the ascorbic acid levels resulting in plasma and white blood cells when ascorbic acid alone is administered. The results of this example also show that administration of Formulation IX causes an increase in NK cell activity with substantially no suppression of NK cell activity from zero to four hours post-administration of Formulation IX. The avoidance of the transient suppression of NK cell activity is very desirable.

EXAMPLE 12

This example shows the effect of administering a formulation of the present invention on NK cell activity and on ascorbic acid levels in both plasma and cells. The formulation in this example is that which is set forth in Table B as Formulation X. Healthy subjects are randomly selected for this example and half of the subjects are given Formulation X while the other subjects are given a biologically equivalent amount of ascorbic acid alone. The results of this example show that administration of Formulation X provides increased ascorbic acid levels in plasma and white blood cells over the ascorbic acid levels resulting in plasma and white blood cells when ascorbic acid alone is administered. The results of this example also show that administration of Formulation X causes an increase in NK cell activity with substantially no suppression of NK cell activity from zero to four hours post-administration of Formulation X. The avoidance of the transient suppression of NK cell activity is very desirable.

TABLE B

| INGREDIENTS (g per kg of finished product powder) | FORMULATION NUMBER | | | | | | | | | |
|---|---|---|---|---|---|---|---|---|---|---|
| | I | II | III | IV | V | VI | VII | VIII | IX | X |
| ascorbic acid | 103.8 | 173.3 | 801.6 | 200.0 | — | 270.0 | 637.0 | — | 107.0 | 78.3 |
| niacinamide ascorbate | 213.5 | — | — | 400.0 | — | — | — | — | 214.0 | 210.0 |
| ascorbyl palmitate | 22.6 | 38.1 | — | 75.0 | 100.0 | — | — | 90.0 | 3.0 | 22.0 |
| ascorbyl arachidonate | — | — | — | — | — | — | — | — | 3.0 | — |
| ascorbyl stearate | — | — | — | — | — | — | — | — | 3.0 | — |
| ascorbyl linoleate | — | — | — | — | — | — | — | — | 3.0 | — |
| ascorbyl linoleneate | — | — | — | — | — | — | — | — | 3.0 | — |
| ascorbyl oleate | — | — | — | — | — | — | — | — | 3.0 | — |
| ascorbyl acetate | — | — | — | — | — | — | — | — | 3.0 | — |
| ascorbyl butyrate | — | — | — | — | — | — | — | — | 3.0 | — |
| calcium ascorbate | 322.1 | 554.6 | — | 100.0 | 250.0 | — | — | 675.0 | 319.0 | 220.0 |
| magnesium ascorbate | 43.2 | 72.1 | — | 100.0 | 75.0 | — | — | 80.0 | 43.0 | 42.0 |
| potassium ascorbate | 19.7 | 32.9 | — | 40.0 | 60.0 | — | — | 35.0 | 20.0 | 19.0 |
| sodium ascorbate | 76.7 | 129.0 | — | 40.0 | 90.0 | — | — | 120.0 | 77.0 | 77.0 |
| manganese ascorbate | — | — | — | 5.0 | 40.0 | 40.0 | 40.0 | — | — | 0.5 |
| zinc ascorbate | — | — | — | 10.0 | 70.0 | 220.0 | 147.0 | — | — | 1.0 |
| iron ascorbate | — | — | — | 5.0 | 7.0 | 220.0 | 147.0 | — | — | 1.0 |
| copper ascorbate | — | — | — | 10.0 | 5.0 | 15.0 | 1.0 | — | — | 100.0 |
| boron ascorbate | — | — | — | 10.0 | 140.0 | 200.0 | 20.0 | — | — | 0.2 |
| molybdenum ascorbate | — | — | — | 2.5 | 3.0 | 15.0 | 3.0 | — | — | 1.0 |
| chromium ascorbate | — | — | — | 2.5 | 5.0 | 20.0 | 5.0 | — | — | 25.0 |
| l-lysine acetate | 33.9 | — | — | — | 5.0 | — | — | — | 12.0 | — |
| arginine | — | — | 33.9 | — | — | — | — | — | — | 20.0 |
| histidine | — | — | — | — | — | — | — | — | 22.0 | 20.0 |
| xylitol | 113.2 | — | — | — | — | — | — | — | — | 37.0 |
| l-xylonic acid | — | — | 113.2 | — | — | — | — | — | — | 25.0 |
| l-lyxonic acid | — | — | — | — | 100 | — | — | — | — | 25.0 |
| 2,3 diketo-l-gulonic acid | — | — | — | — | — | — | — | — | 111.0 | 25.0 |
| hesperidin | 22.6 | — | — | — | — | — | — | — | 11.0 | 6.0 |
| rutin | — | — | 12.6 | — | — | — | — | — | 6.0 | 6.0 |
| proanthocyanidins | — | — | — | — | 10.0 | — | — | — | 3.0 | 8.0 |
| flavonols | — | — | 10.0 | — | — | — | — | — | — | — |
| methoxyflavonols | — | — | — | — | 10.0 | — | — | — | 3.0 | 3.0 |
| alpha-d-ribofuranose | 9.1 | — | 9.1 | — | 10.0 | — | — | — | 9.0 | 9.0 |
| l-cysteine | 6.4 | — | — | — | — | — | — | — | 3.0 | 3.0 |
| cystine | — | — | 6.4 | — | — | — | — | — | 3.0 | — |
| methionine | — | — | — | — | 6.0 | — | — | — | — | 3.0 |
| tetrasodium pyrophosphate | 10.0 | — | 10.0 | — | 8.0 | — | — | — | 10.0 | 10.0 |
| glutathione (reduced) | 3.2 | — | 3.2 | — | 6.0 | — | — | — | 3.0 | 3.0 |
| Total | 1000 | 1000 | 1000 | 1000 | 1000 | 1000 | 1000 | 1000 | 1000 | 1000 |

From the forgoing, it will be appreciated that the preferred formulations of the present invention enhance NK cell cytotoxic activity without the transient suppression or inhibition of NK cell activity which results after administration of ascorbic acid alone. The present invention does not produce any significant change in total NK cell population. Administration of the present invention does result in increased uptake of ascorbic acid into peripheral blood leukocytes with peak uptake of the present invention being up to about 18–25 percent better than when ascorbic acid alone is administered.

The present invention provides an improved ascorbic acid composition and method of administering the same which results in more rapid uptake and utilization of ascorbic acid by human tissue. The present invention also provides a composition including ascorbic acid which provides more desirable overall effect on the human immune system than that provided by ascorbic acid alone and which enhances the activity of human natural killer immune cells. The present invention also provides an ascorbic acid composition and method of administering the same which provides prolonged beneficial effects and results in better uptake by human tissue beyond that obtained when ascorbic acid alone is administered.

The present invention may be embodied in other specific forms without departing from its spirit or essential characteristics. The described formulations are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dietary ascorbic acid supplement composition providing enhanced human immune system activity with substantially no post administration transient suppression of human NK immune cell activity, the ascorbic acid supplement comprising:

a water soluble form of ascorbic acid selected from the group consisting of ascorbic acid, biologically acceptable mineral salts of ascorbic acid, niacinamide ascorbate and mixtures thereof;

a fat soluble ascorbyl ester selected from the group consisting of ascorbyl palmitate, ascorbyl arachidonate, ascorbyl stearate, ascorbyl linoleate, ascorbyl linoleneate, ascorbyl oleate, ascorbyl acetate, ascorbyl butyrate, and mixtures thereof, wherein the weight ratio between said water soluble form of ascorbic acid and said fat soluble ascorbyl ester is between about 50:1 and about 5:1; and at least one ascorbic acid metabolite selected from the group consisting of basic amino acids, metabolic by-products of ascorbic acid breakdown, flavonoid, sulfur containing amino acids, tetrasodium pyrophosphate, and glutathione.

2. A dietary ascorbic acid supplement composition according to claim 1 wherein the weight ratio between said water soluble form of ascorbic acid and said fat soluble ascorbyl ester is between about 40:1 and about 10:1.

3. A dietary ascorbic acid supplement composition according to claim 1 wherein the water soluble form of ascorbic acid contains a mineral salt of ascorbic acid which comprises at least one alkali metal ion salt of ascorbic acid and at least one alkaline earth metal ion salt of ascorbic acid.

4. A dietary ascorbic acid supplement composition according to claim 3 wherein the alkali metal ion salt of ascorbic acid is a member selected from the group consisting of sodium ascorbate and potassium ascorbate and mixtures thereof and wherein the alkaline earth metal ion salt of ascorbic acid is a member selected from the group consisting of calcium ascorbate and magnesium ascorbate and mixtures thereof.

5. A dietary ascorbic acid supplement composition according to claim 4 wherein the water soluble form of ascorbic acid additionally contains a member selected from the group consisting of ascorbic acid and niacinamide ascorbate.

6. A dietary ascorbic acid supplement composition according to claims 4 or 5 wherein the water soluble form of ascorbic acid contains calcium ascorbate, magnesium ascorbate, sodium ascorbate and potassium ascorbate wherein the weight ratio of the alkaline earth metal ion salt of ascorbic acid to alkali metal ion salt of ascorbic acid is between about 2:1 and 6:1, the weight ratio of calcium ascorbate to magnesium ascorbate is between 1:1 and 10:1 and the weight ratio of sodium ascorbate to potassium ascorbate is between about 1:1 and 6:1.

7. A dietary ascorbic acid supplement composition according to claim 6 wherein the water soluble form of ascorbic acid additionally contains a member selected from a group consisting of manganese ascorbate, zinc ascorbate, iron ascorbate, copper ascorbate, phosphorus ascorbate, boron ascorbate, molybdenum ascorbate, chromium ascorbate, and mixtures thereof.

8. A dietary ascorbic acid supplement composition according to claim 6 wherein the weight ratio of water soluble forms of ascorbic acid selected from the group consisting of mineral salts of ascorbic acid and niacinamide ascorbate to ascorbic acid is between about 3:1 to 10:1.

9. A dietary ascorbic acid supplement composition according to claim 6 wherein the weight ratio of the alkaline earth metal ion salt of ascorbic acid to alkali metal ion salt of ascorbic acid is between about 3:1 and 5:1, the weight ratio of calcium ascorbate to magnesium ascorbate is between 5:1 and 8:1 and the weight ratio of sodium ascorbate to potassium ascorbate is between about 3:1 and 5:1.

10. A dietary ascorbic acid supplement composition according to claim 9 wherein the weight ratio of water soluble forms of ascorbic acid selected from the group consisting of mineral salts of ascorbic acid and niacinamide ascorbate to ascorbic acid is between about 5:1 to 8:1.

11. A dietary ascorbic acid supplement composition according to claim 1 wherein said fat soluble ascorbyl ester is ascorbyl palmitate.

12. A dietary ascorbic acid supplement composition according to claim 6 wherein said fat soluble ascorbyl ester is ascorbyl palmitate.

13. A dietary ascorbic acid supplement composition according to claim 7 wherein said fat soluble ascorbyl ester is ascorbyl palmitate.

14. A dietary ascorbic acid supplement composition according to claim 8 wherein said fat soluble ascorbyl ester is ascorbyl palmitate.

15. A dietary ascorbic acid supplement composition according to claim 9 wherein said fat soluble ascorbyl ester is ascorbyl palmitate.

16. A dietary ascorbic acid supplement composition according to claim 10 wherein said fat soluble ascorbyl ester is ascorbyl palmitate.

17. A dietary ascorbic acid supplement according to claim 1 wherein the weight ratio between said water soluble form of ascorbic acid and said fat soluble ascorbyl ester, combined together, and said ascorbic acid metabolite is between about 1000:1 and about 2:1.

18. A dietary ascorbic acid supplement composition according to claim 17 wherein said basic amino acids comprise at least one member selected from the group consisting of lysine; arginine; histidine; and glycine and their acid addition salts and mixtures thereof.

19. A dietary ascorbic acid supplement composition according to claim 17 wherein said flavonoids comprise at least one member selected from the group consisting of hesperidin; proanthocyanidins; rutin; flavonols; and methoxyflavonols.

20. A dietary ascorbic acid supplement composition according to claim 17 wherein said metabolic by-products of ascorbic acid breakdown comprise at least one member selected from the group consisting of xylitol; α-d-ribofuranose; ribose; and d-ribose-5-phosphoric acid.

21. A dietary ascorbic acid supplement composition according to claim 17 wherein said sulfur containing amino acids comprise at least one member selected from the group consisting of cysteine; cystine; and methionine.

22. A dietary ascorbic acid supplement composition according to claim 17 wherein said ascorbic acid metabolite comprises a basic amino acid, a metabolic by-product of ascorbic acid breakdown; a flavonoid; a sulfur containing amino acid; tetrasodium pyrophosphate; and glutathione.

23. A dietary ascorbic acid supplement composition according to claim 22 wherein said basic amino acid is lysine, said metabolic by-product of ascorbic acid breakdown is ribofuranose and xylitol, said bioflavonoid is hesperidin, said sulfur containing amino acid is cysteine.

24. A dietary ascorbic acid supplement composition according to claim 23 wherein, relative to glutathione, the weight ratio of lysine is between about 7:1 and 13:1, the weight ratio of α-d-ribofuranose is between about 1.5:1 and 4:1, the weight ratio of xylitol is between about 25:1 and 45:1, the weight ratio of hesperidin is between about 4:1 and 10:1, the weight ratio of cysteine is between about 1:1 and 3:1, and the weight ratio of tetrasodium phosphate is between about 2:1 and 4:1.

25. A method of administering ascorbic acid to a human with substantially no post administration transient suppression of human NK immune cell activity which comprises administering to a human an effective amount of a composition comprising:

a water soluble form of ascorbic acid selected from the group consisting of ascorbic acid, biologically acceptable mineral salts of ascorbic acid, niacinamide ascorbate and mixtures thereof; and selected from the group consisting of ascorbyl palmitate, ascorbyl arachidonate, ascorbyl stearate, ascorbyl linoleate, ascorbyl linoleneate, ascorbyl oleate, ascorbyl acetate, ascorbyl butyrate, and mixtures thereof, wherein the weight ratio between said water soluble form of ascorbic acid and said fat soluble ascorbyl ester is between about 50:1 and about 5:1.

26. A method according to claim 25 wherein the weight ratio between said water soluble form of ascorbic acid and said fat soluble ascorbyl ester is between about 40:1 and about 10:1.

27. A method according to claim 25 wherein the water soluble form of ascorbic acid contains a mineral salt of ascorbic acid which comprises at least one alkali metal ion salt of ascorbic acid and at least one alkaline earth metal ion salt of ascorbic acid.

28. A method according to claim 27 wherein the alkali metal ion salt of ascorbic acid is a member selected from the group consisting of sodium ascorbate and potassium ascorbate and mixtures thereof and wherein the alkaline earth metal ion salt of ascorbic acid is a member selected from the group consisting of calcium ascorbate and magnesium ascorbate and mixtures thereof.

29. A method according to claim 28 wherein the water soluble form of ascorbic acid additionally contains a member selected from the group consisting of ascorbic acid and niacinamide ascorbate.

30. A method according to claims 28 or 29 wherein the water soluble form of ascorbic acid contains calcium ascorbate, magnesium ascorbate, sodium ascorbate and potassium ascorbate wherein the weight ratio of the alkaline earth metal ion salt of ascorbic acid to alkali metal ion salt of ascorbic acid is between about 2:1 and 6:1, the weight ratio of calcium ascorbate to magnesium ascorbate is between 1:1 and 10:1 and the weight ratio of sodium ascorbate to potassium ascorbate is between about 1:1 and 6:1.

31. A method according to claim 30 wherein the water soluble form of ascorbic acid additionally contains a member selected from a group consisting of manganese ascorbate, zinc ascorbate, iron ascorbate, copper ascorbate, phosphorus ascorbate, boron ascorbate, molybdenum ascorbate, chromium ascorbate, and mixtures thereof.

32. A method according to claim 30 wherein the weight ratio of water soluble forms of ascorbic acid selected from the group consisting of mineral salts of ascorbic acid and niacinamide ascorbate to ascorbic acid is between about 3:1 to 10:1.

33. A method according to claim 30 wherein the weight ratio of the alkaline earth metal ion salt of ascorbic acid to alkali metal ion salt of ascorbic acid is between about 3:1 and 5:1, the weight ratio of calcium ascorbate to magnesium ascorbate is between 5:1 and 8:1 and the weight ratio of sodium ascorbate to potassium ascorbate is between about 3:1 and 5:1.

34. A method according to claim 33 wherein the weight ratio of water soluble forms of ascorbic acid selected from the group consisting of mineral salts of ascorbic acid and niacinamide ascorbate to ascorbic acid is between about 5:1 to 8:1.

* * * * *